United States Patent [19]

von Bittera et al.

[11] 4,283,400

[45] Aug. 11, 1981

[54] MEDICATED ANIMAL FEED BASED ON LIVER MEAL

[75] Inventors: Miklos von Bittera; Herbert Voege, both of Leverkusen; Reinwalt Bauditz, Wuppertal, all of Fed. Rep. of Germany

[73] Assignee: Bayer Aktiengesellschaft, Leverkusen, Fed. Rep. of Germany

[21] Appl. No.: 73,990

[22] Filed: Sep. 10, 1979

[30] Foreign Application Priority Data

Sep. 25, 1978 [DE] Fed. Rep. of Germany ....... 2841668

[51] Int. Cl.³ .................... A61K 31/43; A61K 31/65; A61K 31/325; A61K 31/495
[52] U.S. Cl. .................................. 424/250; 424/238; 424/270; 424/271; 424/300; 424/320; 426/2; 426/72; 426/102
[58] Field of Search ............... 424/250, 238, 270, 271, 424/320, 300; 426/2, 72, 102

[56] References Cited

U.S. PATENT DOCUMENTS

| 3,883,672 | 5/1975 | Bone et al. | 426/72 |
| 4,153,735 | 5/1979 | Mommer | 426/2 |

OTHER PUBLICATIONS

Morrison, "Feeds and Feeding", pp. 524–525, 548–549 and 952–953, 22nd Ed., The Morrison Publishing Co. NY (1957).

Tixier, Chem. Abstracts, vol. 78, abst. 33919v (1973), (abst. of Ger. Offen. No. 2,202,736).

Feedstuffs (Feed Additive Compendium Issue), pp. 83, 131–132, 240–241, and 248–249, The Miller Publishing Co.

Feed Trade Manual, pp. 34–36.

Mapson et al., Chem. Abstracts, vol. 27, pp. 2736–2737, (1933), (abst. of British Pat. No. 378,399).

Piccioni, Chem. Abstracts, vol. 49, col. 1990 (1955), (abst. of Ital. Pat. No. 477,361).

Ahmad et al., Chem. Abstracts. vol. 75, abst. 138279c (1971).

Harms et al., vol. 50, col. 14142 (1956).

Holmes et al., Chem. Abstracts vol. 29, col. 4802 (1935).

Hiroshi et al., Chem. Abstracts vol. 50, col. 14996 (1956).

*Primary Examiner*—John D. Randolph
*Attorney, Agent, or Firm*—Sprung, Felfe, Horn, Lynch & Kramer

[57] ABSTRACT

The invention relates to the provision of medicated animal feeds comprising one or more pharmaceutically active compounds and liver meal as a formulation auxiliary. Also included in the invention are methods for the use of said animal feeds of the invention.

6 Claims, No Drawings

MEDICATED ANIMAL FEED BASED ON LIVER MEAL

The present invention relates to a medicated animal feed, to a process for its production and to its use in treating animal diseases.

Oral administration of medicaments to animals is frequently associated with great difficulties, especially if these medicaments have an unpleasant, usually bitter, flavour. The medicament administered orally, for example via a medicated feed, is frequently not accepted and the desired oral treatment either cannot be carried out at all or can be carried out under force only to a restricted and thus usually insufficient extent.

In the case of livestock such as cattle and pigs, treatment with medicated feed in a low dosage over a relatively long period is coming more and more into the foreground. In the case of domestic animals such as dogs and cats, such feed additives as a rule are restricted to neutral-testing additives for nutrition and prophylaxis, such as vitamins, trace elements and the like, since medicaments which have an unpleasant taste, especially in the effective single dose, are not taken up by the animals.

There is thus a greatly pronounced need for a medicinal formulation for animals, in particular for domestic animals such as dogs and cats, with the aid of which unpleasant, usually bitter-tasting pharmaceutically active compounds can be administered orally in a problem-free and precisely dosed form, that is to say are taken up voluntarily by the animals.

It has now been found that voluntary oral uptake of the pharmaceutically active compound ("self-intake principle") by the animal to be treated is made possible by using liver meal as a formulation auxiliary.

According to the present invention there is, therefore, provided medicated animal feeds comprising one or more pharmaceutically active compound(s) and liver meal as a formulation auxiliary.

By liver meal there is to be understood a product which is isolated, and ca be extracted, by drying and grinding the fresh liver of warm-blooded land animals. (In this context, see H. J. Entel, N. Förster and E. Hinckers: Futtermittelrecht (Feedstuff Law) FMV-edition, part 1, section 1.1, page 41, Verlag P. Parey (1970/78, date:March 1978). The term "liver meal", as used herein, includes extracted liver meal and defatted liver meal.

A liver meal which fulfills the following requirements is preferably employed: raw proteins: at least 65%, ferment-soluble raw protein: at least 42%, raw fat: at most 18%, sodium chloride: at most 2.5% and water: at most 10%.

Liver meals which deviate slightly from the norm indicated above can also be employed for the preparation of the medicated animal feed according to the invention.

Extracted liver meal is the preferred formulation auxiliary. De-fatted liver meal is particularly preferred.

Liver meal has not hitherto been employed as an auxiliary for medicinal preparations, but certainly as a feed additive. Thus, an extracted liver meal is commercially available under the Trade Mark "Murnil". Liver meal would not have obviously suggested itself as suitable as a pharmaceutical auxiliary since it is very hydrophobic and elastic.

Formation of the active compound or active compound mixture into a medicament with the (preferably extracted and de-fatted) liver meal thus takes place with the addition of a binder (carrier) customary in pharmacy. Preferred possible binders for the preparation of the medicated animal feed based on liver meal are: starch, polyvinylpyrrolidone, gelatin, alkali metal alginates, for example sodium alginate, and cellulose derivatives, such as, for example, methylcellulose and carboxymethylcellulose. The choice of the binder depends, above all, on the formulation to be prepared (for example biscuit form, pellet form or bead form).

According to the present invention there is further provided a process for the production of a medicated animal feed according to the present invention characterized in that a pharmaceutically active compound to be administered (or pharmaceutically active compound mixture) is mixed with the liver meal, a binder, one or more other auxiliaries and water and the pasty mass formed is proportioned and dried. The mixture of active compound(s), liver meal and auxiliary is preferably kneaded with aqueous solution of the binder. The paste-like mass can be proportioned in the most diverse ways customary in the food industry or pharmaceuticals industry to give ready-to-use medicinal forms which are then voluntarily taken up by the animals.

Thus, the mass can, for example, be passed over an extruder and the extrudate cut off such that the piece represents the dose of the medicament for the animal. Biscuits can also be cut out of the rolled-out mass. It is also possible to pass the mass over any desired granulator. In the next process step, the mass is dried, the drying temperature depending on the stability of the active compound to heat. The mass is preferably dried at 30° to 180° C., in particular at 80° to 140° C. It is then packed in the customary manner, the granules being filled as a single dose into, for example, sachets, bags or beakers.

Further auxiliaries which can be employed are stabilizers of all types for the active compound, for example: antioxidants, such as butylhydroxyanisole and sodium meta-bisulphite, preservatives, for example phydroxbenzoic acid esters, sorbic acid and benzoic acid, and also colorants, such as iron oxide pigments and other food colorants, and in addition aroma substances, such as meat aroma, liver aroma and roast aroma.

Possible pharmaceutically active compounds are virtually all the active compounds which can be employed in veterinary medicine, and unpleasant-tasting active compounds which in most cases have a bitter flavour are preferably employed; examples which may be mentioned are: anthelmintic agents, such as praziquantel, tetramisole, febantel, levamisole, niclosamide, piperazine salts, antibiotics, such as chloramphenicol, tetracycline and penicillin derivatives, such as the benzathine salt of penicillin G, amplicillin and cloxacillin, hormones, for example 6-chloro-6-dehydro-17$\zeta$-acetoxyprogesterone.

In the preparation of the medicated animal feed, the following parts of the ingredients indicated above are preferably brought together, the following figures given relating to parts by weight: liver meal: 50 to 99, preferably 85 to 98, pharmaceutically active compound (or pharmaceutically active compound mixture): 0.1 to 20, preferably 0.5 to 10, binder: 1 to 20, preferably 2 to 10, and other auxiliaries: 0.01 to 5, preferably 0.1 to 2.

10 to 60, preferably 30 to 50, parts by weight of water, which is removed again by drying after forming the paste, are added per 100 parts by weight of the above mixture of solids.

The constituents are then preferably present in the finished liver meal preparation according to the invention (medicated animal feed based on liver meal) in the ranges indicated above.

The present invention further relates to the treatment of animal diseases comprising administering orally to the animal an appropriate medicated animal feed according to the present invention.

It is possible, by the process according to the invention, for the preparation of the medicated animal feed based on liver meal, to realize an exact dosage of the medicament by appropriate admixing of the active compound to be administered and proportioning of the medicinal form to be administered, so that an exact amount of the medicated feed can be given as a function of the weight of the animal to be treated. In this context, see also the individual dosages indicated in the Examples which follow with respect to some active compounds.

The following Examples which are illustrative but not limitative of the invention, illustrate the preparation of medicated animal feed according to the present invention and illustrate the use of such medicated animal feed.

EXAMPLE 1

980.0 g of de-fatted liver meal are mixed with 10.0 g of praziquantel active compound of the formula

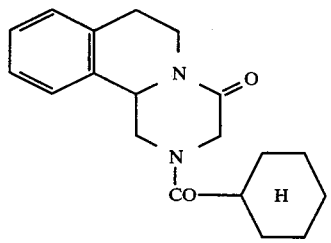

The mixture is kneaded to a paste with a solution of 10.0 g of polyvinylpyrrolidone 25 in 500.0 g of water.

The paste is rolled out in the conventional manner and pieces which, after drying, weigh 5 g and thus contain 50 mg of praziquantel active compound are separated from the rolled-out paste. (This corresponds to an effective dose for a dog weighing 10 kg). The pieces of paste are dried in a drying cabinet at 50° C.

EXAMPLE 2

10 dogs (body weight: 8.5 to 10.2 kg) were in each case offered a conventional tablet containing 50 mg of praziquantel, a preparation, produced according to Example 1, containing 50 mg of praziquantel and liver meal, and a conventional tablet containing 50 mg of praziquantel, which was aromatised with liver aroma.

Whilst the preparation produced according to Example 1 was accepted and eaten by each dog, the conventional tablets and the conventional tablets aromatised with liver aroma were not taken up by the animals.

EXAMPLE 3

1,000 g of de-fatted liver meal are mixed with 7 g of praziquantel active compound and the mixture is moistened with 340 g of a 5.2% strength aqueous sodium alginate mucilage and mixed homogeneously.

The mixture is then passed over a feedstuff pelleting unit on a laboratory scale and pellets with a diameter of 4 mm are prepared. The pellets are dried in a drying cabinet at 50° C. for 4 hours and then filled into containers.

An acceptance test was then carried out on 7 dogs (average weight about 10 kg). All the dogs accepted the pellets prepared according to Example 3.

EXAMPLE 4

500 g of de-fatted liver meal are mixed with 10 g of levamisol hydrochloride (L-2,3,5,6-tetrahydro-6-phenylimidazo[2,1-b]thiazole hydrochloride) and 0.5 g of sodium metabisulphite (antioxidant) and the mixture is moistened with 170 g of a 5.2% strength aqueous sodium alginate mucilage and mixed homogeneously.

The mixture is then worked up to pellets (diameter: 4 mm) as described in Example 3.

Of each case 10 dogs of different species, to which commercially available levamison hydrochloride tablets, pharmaceutical granules based on glucose and containing levamisol hydrochloride and liver meal pellets prepared according to Example 4 were offered, 9 took up the medicament prepared according to Example 4, whilst in the other two groups, only one dog took up one tablet but no dogs took up the granules based on glucose.

EXAMPLE 5

(A) 950.0 g of liver meal are mixed homogeneously with 10.0 g of praziquantel active compound.

(B) 30.0 of polyvinylpyrrolidone 25 are dissolved in 500.0 g of water together with 10.0 g of lecithin.

The homogeneous mixture according to (A) is kneaded to a paste with the solution according to (B).

The paste is rolled out as described in Example 1 and pieces which, after drying, contain 5 g of praziquantel are separated from the rolled-out paste.

The preparation according to Example 5 was placed before 10 dogs and taken up by all of them.

Example 6

990 g of de-fatted liver meal are mixed homogeneously with 5.0 g of chloramphenical—an active compound with an unpleasant bitter taste.

The mixture is kneaded to a paste with a solution of 10.0 g of polyvinylpyrrolidone 25 in 500.0 g of water and the paste is processed to biscuits as described in Example 1. 10 g of liver meal biscuits according to Example 6 were offered per 5 kg of body weight of the dogs. Of a total of 10 dogs, 8 take up the biscuits. In contrast, a piece of a commercially available chloramphenicol bolus offered for comparison was refused.

EXAMPLE 7

10.0 g of praziquantel active compound, 20.0 g of soluble starch and 970.0 g of de-fatted liver meal are moistened with 300 ml of water and the mixture is kneaded thoroughly. The mass thus obtained is coarsely comminuted into 5 mm pieces using a shredder and dried gently for 5 hours at 50° C. in a drying cabinet. The granules obtained are placed before 10 dogs, in portions of 5.0 g of granules per 10 kg of dog weight. 10 other dogs were offered a corresponding number of conventional tablets granulated with lactose and starch.

The liver meal granules according to Example 7 were taken up by 9 of the animals, the tablets were taken up by none of the animals.

What is claimed is:

1. A medicated animal feed comprising 0.1 to 20 parts by weight of one or more pharmaceutically active compounds selected from the group consisting of anthelmintic agents, praziquantel, tetramisole, febantel, levamisole, niclosamide, piperazine salts, chloramphenicol, tetracycline, penicillin derivatives, ampicillin, cloxacillin and 6-chloro-6-dehydro-17α-acetoxy-progesterone, 1 to 20 parts by weight of a binder selected from the group consisting of starch, polyvinylpyrrolidone, gelatin, sodium alginate and a cellulose derivative, 50 to 99 parts by weight liver meal as a formulation auxiliary and 0.04 to 5 parts by weight of one or more other auxiliaries.

2. A medicated animal feed according to claim 1, characterized in that the liver meal is de-fatted liver meal.

3. A medicated animal feed according to claim 1, characterized in that the dry mass to be administered contains 85 to 98 parts by weight of liver meal, 0.5 to 10 parts by weight of pharmaceutically active compound or compounds 2 to 10 parts by weight of binder and 0.1 to 2 parts by weight of one or more other auxiliaries.

4. A medicated animal feed according to claim 1, characterized in that the liver meal is de-fatted liver meal and that the active compound is Praziquantel.

5. A medicated animal feed according to claim 1, characterized in that the liver meal is de-fatted liver meal and that the active compound is levamisole-hydrochloride.

6. A medicated animal feed according to claim 1, characterized in that the liver meal is de-fatted liver meal and that the active compound is chloramphenicol.

* * * * *